(12) United States Patent
Spriesterbach et al.

(10) Patent No.: US 11,596,811 B2
(45) Date of Patent: Mar. 7, 2023

(54) RADIOTHERAPY CONTROL SYSTEM

(71) Applicant: Elekta Limited, Crawley (GB)

(72) Inventors: Ralf Spriesterbach, Crawley (GB); Paul Berwick, Crawley (GB); Adrian Smith, Crawley (GB); Paul Boxall, Crawley (GB)

(73) Assignee: Elekta Limited, Crawley (GB)

( * ) Notice: Subject to any disclaimer, the term of this patent is extended or adjusted under 35 U.S.C. 154(b) by 0 days.

(21) Appl. No.: 17/041,071

(22) PCT Filed: Mar. 26, 2019

(86) PCT No.: PCT/EP2019/057651
§ 371 (c)(1),
(2) Date: Sep. 24, 2020

(87) PCT Pub. No.: WO2019/185669
PCT Pub. Date: Oct. 3, 2019

(65) Prior Publication Data
US 2021/0093894 A1     Apr. 1, 2021

(30) Foreign Application Priority Data
Mar. 26, 2018   (GB) ...................................... 1804825

(51) Int. Cl.
*A61N 5/10*         (2006.01)
(52) U.S. Cl.
CPC ........... *A61N 5/1081* (2013.01); *A61N 5/107* (2013.01); *A61N 5/1049* (2013.01);
(Continued)

(58) Field of Classification Search
CPC ........ A61N 5/10; A61N 5/103; A61N 5/1042; A61N 5/1048; A61N 5/1064;
(Continued)

(56) References Cited

U.S. PATENT DOCUMENTS

| 5,554,848 A | 9/1996 | Hermony et al. |
| 6,035,228 A * | 3/2000 | Yanof ..................... A61B 90/11 606/130 |

(Continued)

FOREIGN PATENT DOCUMENTS

| DE | 102008015589 A1 * | 9/2008 | ............. H04N 19/12 |
| GB | 2491363 | 12/2012 | |

(Continued)

OTHER PUBLICATIONS

International Search Report in corresponding PCT Application No. PCT/EP2019/057651 dated Jun. 28, 2019 (3 pages).

(Continued)

*Primary Examiner* — Courtney D Thomas
(74) *Attorney, Agent, or Firm* — Schwegman Lundberg & Woessner, P.A.

(57) ABSTRACT

A radiotherapy system, comprising: a patient support, a radiation beam generator, a gantry on which the radiation beam generator is mounted, the gantry being moveable so as to rotate the radiation beam generator around the patient support, and a control system including a real-time control system mounted on the gantry and configured to provide real-time control signals to the patient support, the radiation beam generator, and the gantry.

14 Claims, 4 Drawing Sheets

(52) U.S. Cl.
CPC .... *A61N 5/1067* (2013.01); *A61N 2005/1055* (2013.01); *A61N 2005/1074* (2013.01)

(58) Field of Classification Search
CPC ...... A61N 5/1065; A61N 5/1067–1069; A61N 5/107; A61N 5/1071; A61N 5/1075; A61N 2005/1054; A61N 2005/1061; A61N 2005/1074; A61B 6/03; A61B 6/46; A61B 6/467; A61B 6/52; A61B 6/54; A61B 6/542; A61B 6/548; A61B 6/56; A61B 6/563; A61B 6/566; A61B 34/10; A61B 34/20; A61B 34/25; A61B 34/37; A61B 2034/2074; A61B 2560/0266; A61B 2560/0271; H05G 1/08; H05G 1/085; H05G 1/10; H05G 1/56; G01N 2223/304; G01N 2223/306; G01N 2223/419

See application file for complete search history.

(56) References Cited

U.S. PATENT DOCUMENTS

| | | | |
|---|---|---|---|
| 7,869,859 B2* | 1/2011 | Shinno | A61B 6/465 378/98 |
| 2011/0080990 A1 | 4/2011 | Filiberti et al. | |
| 2011/0150171 A1* | 6/2011 | Breuer | A61B 6/56 378/91 |
| 2014/0070115 A1 | 3/2014 | Oster et al. | |
| 2016/0367207 A1 | 12/2016 | Michaud et al. | |
| 2019/0150876 A1* | 5/2019 | Kagermeier | A61B 6/06 |

FOREIGN PATENT DOCUMENTS

| | | | | |
|---|---|---|---|---|
| GB | 2507792 | 5/2014 | | |
| GB | 2572337 | 10/2019 | | |
| GB | 2572337 | 10/2020 | | |
| JP | 2007313310 A | * 12/2007 | ........... | A61B 5/7475 |
| WO | WO 2011-039624 | 4/2011 | | |
| WO | WO 2012-077064 | 6/2012 | | |
| WO | WO 2014-043172 | 3/2014 | | |
| WO | WO 2015-103564 | 7/2015 | | |
| WO | WO 2018-093933 | 5/2018 | | |
| WO | 2019185669 | 10/2019 | | |

OTHER PUBLICATIONS

UK Search Report in corresponding UK Application No. GB 1804825.6 dated Aug. 30, 2018 (3 pages).
"International Application Serial No. PCT EP2019 057651, Written Opinion dated Jun. 28, 2019", 5 pgs.
"International Application Serial No. PCT EP2019 057651, International Preliminary Report on Patentability dated Oct. 8, 2020", 7 pgs.
"United Kingdom Application Serial No. 1804825.6, Response filed May 26, 2020 to Combined Search and Examination Report under Sections 17 and 18(3) dated Aug. 30, 2018", 12 pgs.
"United Kingdom Application Serial No. 1804825.6, Preliminary Examination Report dated Apr. 16, 2018", 2 pgs.
"United Kingdom Application Serial No. 1804825.6, Intention to Grant dated Jul. 29, 2020", 2 pgs.

* cited by examiner

RADIOTHERAPY CONTROL SYSTEM

CROSS-REFERENCE TO RELATED PATENT APPLICATIONS

This is a National Phase of International Application No. PCT/EP2019/057651, filed Mar. 26, 2019, which claims the benefit of United Kingdom Application No. 1804825.6 filed Mar. 26, 2018. The entire contents of the above-referenced applications are expressly incorporated herein by reference.

FIELD OF THE INVENTION

The present invention relates to control systems for controlling radiotherapy apparatus. In particular, the invention relates to aspects of real-time control during operation.

BACKGROUND ART

A known type of radiotherapy system is shown in FIG. 1, and comprises a patient support 10, often called a table or couch, which is moveable in the longitudinal direction x-x and in the vertical direction z-z. A rotatable gantry 12 is mounted in the room containing the table 10, so as to extend over the table 10. The gantry 12 carries a radiotherapy beam generator 14 that can project a radiotherapy beam at the table 10. The gantry 12 is mounted so that it can be rotated around the longitudinal axis x-x. In this way, the radiotherapy beam can be directed at the table from any direction. A control system 16 provides control signals to the gantry 12, radiotherapy beam generator 14 and table 10. By providing real-time control signals, the control system 16 can dynamically modulate operation of the system, such as the beam generation and shaping, rotation of the gantry 12, and movement of the table 10. In this way, a patient 2 having a tumour to be treated by radiotherapy can be provided with a treatment in which the shape of the radiotherapy beam is matched to the shape of the tumour, or part of the tumour, and the radiotherapy beam can be directed at the tumour from a number of different rotational positions. This can be used to optimise the radiation dose received by the tumour while minimising irradiation of healthy tissue.

The configuration of the control system, and in particular the connections providing real-time control signals typically limits the gantry to one complete rotation in any direction, after which it must be reset by counter-rotating in the opposite direction.

This invention addresses the need for a control system that can be used with various gantry configurations, and that can alleviate the restriction on the number of rotations of the gantry during a treatment process.

SUMMARY OF THE INVENTION

One aspect of the invention provides a radiotherapy system, comprising a patient support, a radiation beam generator, a gantry on which the radiation beam generator is mounted, the gantry being moveable so as to rotate the radiation beam generator around the patient support, and a control system including a real-time control system mounted on the gantry and configured to provide real-time control signals to the patient support, the radiation beam generator, and the gantry.

The control system can also include an off-gantry control system mounted separately from the gantry and configured to exchange control signals with the real-time control system mounted on the gantry.

The gantry can comprise an annular structure having a bore thought which the patient support can extend, and that is rotatable through more than 360° in either direction. The annular gantry can include one or more slip rings through which power is provided for the radiation beam generator, and any other powered components mounted on the gantry, and which can also provide a data link with the real-time control system mounted on the gantry. The gantry can include separate slip rings for power and data.

The system can further comprise a wireless data connection between the real-time control system and the off-gantry control system.

The off-gantry control system can include a treatment planning system that is configured to provide real-time control routines for implementation by the real-time control system mounted on the gantry.

The real-time control system can be configured to control generation and shaping of the beam generated by the radiation beam generator.

A fibre-optic link can be provided between the off-gantry control system and the patient support to provide the real-time control signals.

The off-gantry control system can include a gantry drive controller for controlling rotation of the gantry, wherein the real-time control system is configured to provide control signals to the gantry drive controller.

An imaging system can be provided on the gantry for obtaining images of a patient during treatment with the radiotherapy beam, the real-time control system being configured to provide control signals to the imaging system.

Other aspects of the invention will be apparent from the following description.

BRIEF DESCRIPTION OF THE DRAWINGS

The invention will now be described by way of example and with reference to the accompanying figures in which.

DETAILED DESCRIPTION OF THE EMBODIMENTS

Figure 2:
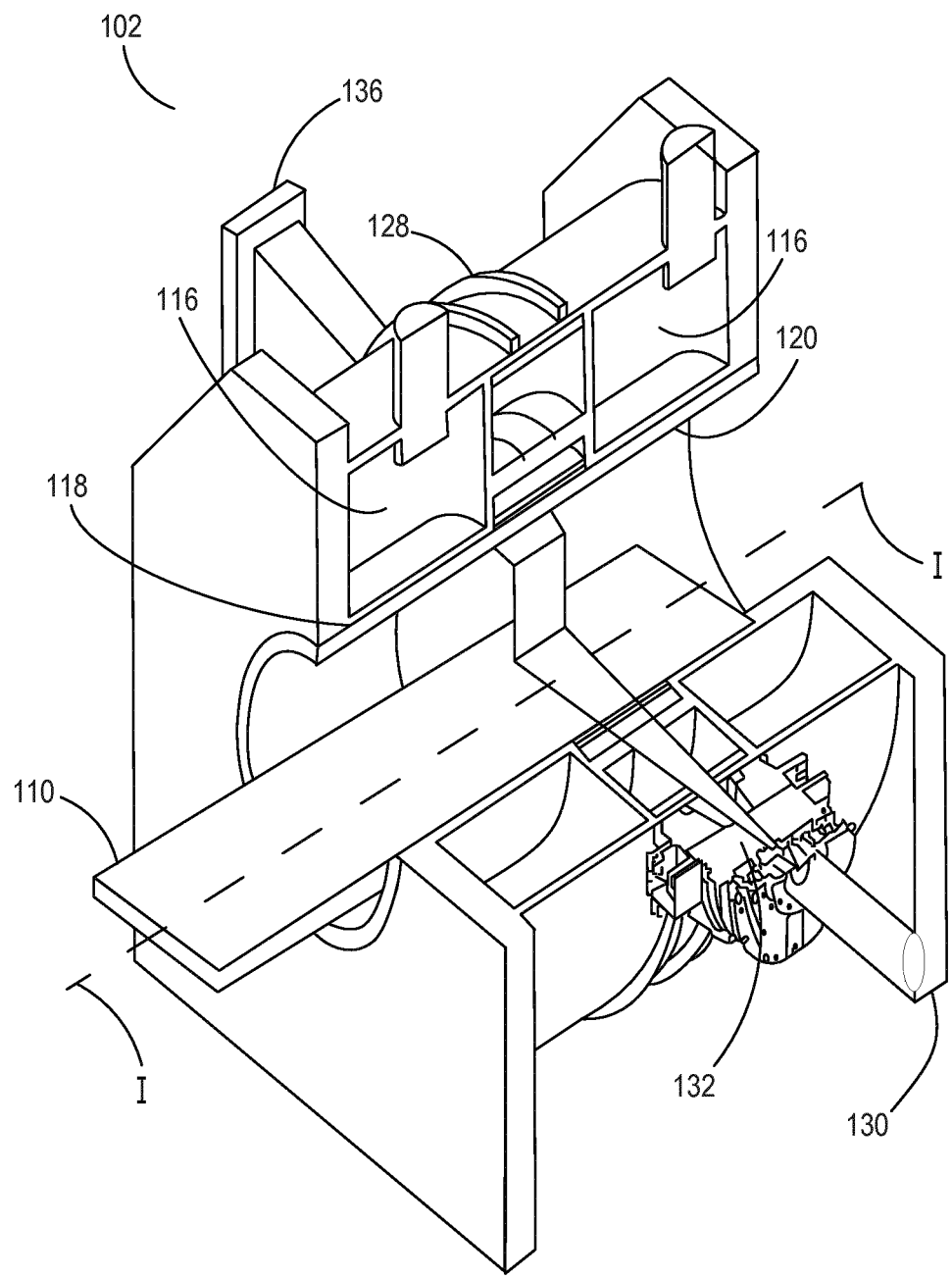
FIG. 2 is a combined radiotherapy and MRI system.

FIG. 2 shows a system comprising a radiotherapy apparatus and a magnetic resonance imaging (MRI) apparatus. The radiotherapy apparatus 106 and MRI apparatus 104 are shown schematically in FIG. 3.

The system includes a patient support or couch 110, for supporting a patient in the apparatus. The couch 110 is movable along a horizontal, translation axis (labelled "I"), such that a patient resting on the couch is moved into the radiotherapy and MRI apparatus as described in WO 2009/007737.

Figure 3:
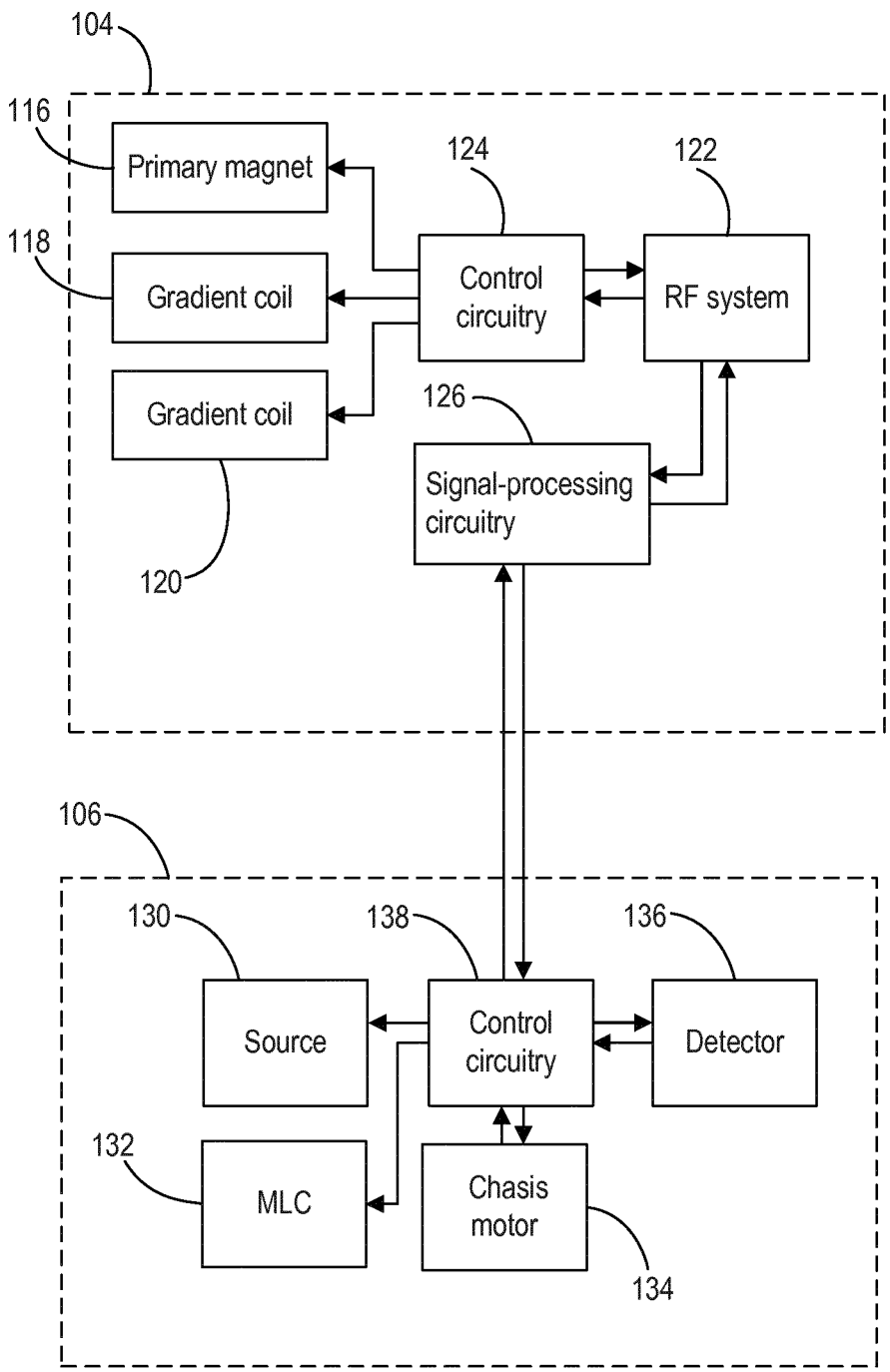
FIG. 3 shows a general schematic of the control system of the system of FIG. 2.

The system 102 (comprising an MRI apparatus 104 and a radiotherapy apparatus 106, as shown in FIG. 3) can be used for producing real-time images of a patient positioned on the couch 110. The MRI apparatus includes a primary magnet 116 which acts to generate the primary magnetic field for magnetic resonance imaging. The magnetic field lines generated by the magnet 116 run substantially parallel to the central translation axis I. The primary magnet 116 comprises one or more coils with an axis that runs parallel to the translation axis I. The one or more coils may be a single coil or a plurality of coaxial coils of different diameter, as illustrated. The coil(s) in the primary magnet 116 is arranged such that a central window of the magnet 116 is free of coils. The magnet 116 may further comprise one or more active shielding coils, for generating a magnetic field outside the magnet 116 of approximately equal magnitude and opposite polarity to the primary magnetic field. The more sensitive parts of the system 102, such as the accelerator, are positioned in this region outside the magnet 116 where the magnetic field is cancelled, at least to a first order. The MRI apparatus 104 further comprises two gradient coils 118, 120, which generate the gradient magnetic field that is superposed on the primary magnetic field. These coils 118, 120 generate a gradient in the resultant magnetic field that allows spatial encoding of the protons so that their position can be determined from the frequency at which resonance occurs (the Larmor frequency). The gradient coils 118, 120 are positioned around a common central axis with the primary magnet 116, and are displaced from one another along that central axis. This displacement creates a gap, or window, between the two coils 118, 120. In an embodiment where the primary magnet 116 also comprises a central window between coils, the two windows are aligned with one another.

An RF system 122 transmits radio signals at varying frequencies towards the patient, and detects the absorption at those frequencies so that the presence and location of protons in the patient can be determined. The RF system 122 may include a single coil that both transmits the radio signals and receives the reflected signals, dedicated transmitting and receiving coils, or multi-element phased array coils, for example. Control circuitry 124 controls the operation of the various coils 116, 118, 120 and the RF system 122, and signal-processing circuitry 126 receives the output of the RF system, for generating images of the patient supported by the couch 110.

The system 102 further comprises a radiotherapy system 106 which delivers doses of radiation to a patient supported by the couch 110. The majority of the radiotherapy apparatus 106, including at least a radiation beam generator 130 (e.g. an x-ray source) is mounted on a gantry or chassis 128. The gantry 128 is an annular structure having a bore into which the couch 110 can extend, and is continuously rotatable around the couch 110 when it is inserted into the treatment area, powered by one or more gantry/chassis motors 134. In the illustrated embodiment, a radiation detector 136 is also mounted on the gantry 128 opposite the radiation beam generator 130 and with the rotational axis of the gantry positioned between them. The gantry 128 is arranged such that it can be rotated through more than 360 degrees in any direction, a slip ring being provided to allow power to be provided to the components mounted on the gantry 128.

Figure 4:
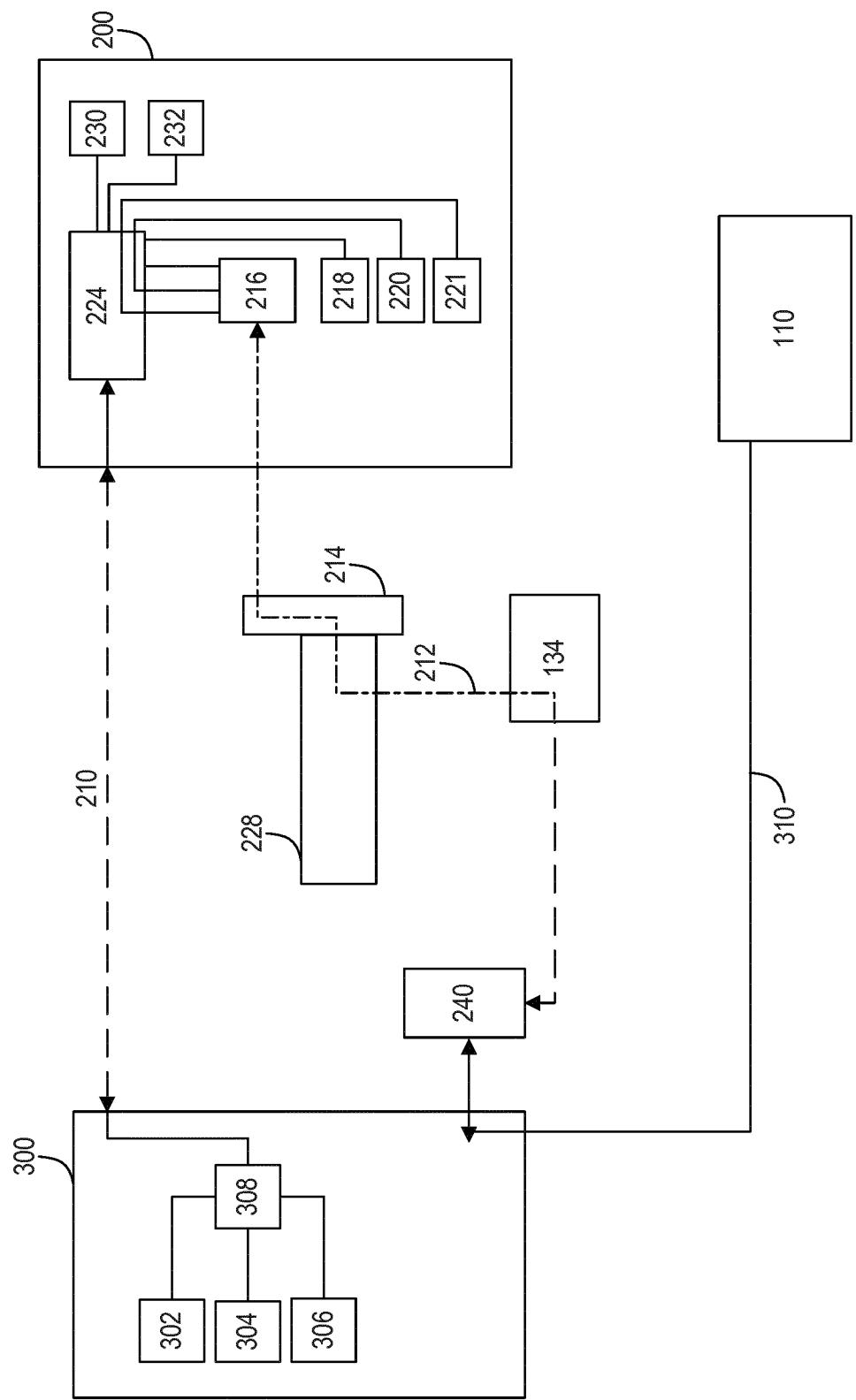
FIG. 4 shows further detail of the control system.

The control circuitry 138 of the radiotherapy system 106 shown in FIG. 3 further comprises a control system shown schematically in FIG. 4. The control system comprises two main sections: an on-gantry system 200 that is mounted on the gantry 128 so as to rotate with it, and an off-gantry system 300 that is mounted separately from the gantry 128. Two data connections are provided between the on-gantry system and off-gantry system: a wireless data link 210, and a hardwire link 212 that provides a data signal path that extends through the slip ring 214 on the gantry 128. The slip ring 214 can comprise one or more separate rings, and individual rings can be used for power or data transmission (or both). For example, two slip rings can be provided, one for data and the other for power.

The on-gantry system 200 includes a real-time controller 216 that is responsible for providing real-time (RT) control signals to the various functional components of the radiotherapy system 106, located both on-gantry and off-gantry. As examples of on-gantry components under RT control, various dynamic operational aspects of the radiation beam generator 130 are under the control of the RT controller 216. These include aspects such as electron gun control, RF modulation, etc. that affect the radiation source output 218, and beam shaping aspects 220, such as control the positioning of leaves of of a multi-leaf collimator (MLC) 132, or positioning of diaphragm blocks.

As examples of off-gantry components under on-gantry RT control, the couch 110 is also provided with control signal 221 from the RT controller 216 so that its movement in the bore of the gantry can be coordinated with operation of the radiation generator and beam shaping system, and the gantry motors 134 are also under RT control from the RT controller 216, acting to rotate the gantry 128 to position the radiation generator at different azimuthal positions around the couch 110.

The RT controller 216 can be programmed to store sets of control signals for operation of the various system components. Because several on-gantry components under real time control require both accurate time synchronization of control signals, and relatively high data bandwidth, the RT controller 216 is connected to these components by a hardwire data network, such as an Ethernet network 222. An Ethernet switch 224 can be provided to connect the components 218, 220, 221, etc. to the RT controller 216. While the off-gantry components also require accurate time synchronization of the control signals, the required bandwidth is relatively lower. In this case, the data channel can pass through the slip ring 214, for example by means of a CAN RT network 212 including a CAN bridge 228 located off-gantry. An interface 240 with the off-gantry system 300 is also provided.

Certain on-gantry components do not require "hard" RT control and so can be provided with control signals from the off-gantry system 300 via a Wi-Fi network 210 that interfaces with an associated Ethernet switch 224 on the gantry. Examples of components that can be under such "soft" RT control include a water conditioning system 230 for temperature control of the on-gantry components, general control of an imaging system 232, and non-RT components (not shown). In addition, this network 210 can also be used to upload control routines to the RT controller 216 for hard RT control.

The off-gantry system 300 can also include other subsystems dedicated to functions that are not used for direct RT control of the system such as a treatment planning system 302 for generating the control routines to be sent to the RT controller 216, data processing systems 304, imaging systems 306, etc. All of these can be connected by an Ethernet network 308 using hardwire or Wi-Fi connections.

Because the couch 110 is located within the high magnetic field regions of the MRI apparatus 104, the control signals can be provided by means of an optical fibre connection 310. The off-gantry system 300 can be located in a separate room from the gantry 128 and from the treatment room containing the couch 110.

Operation of the MRI system 104 can be conducted essentially separately of the operation of the radiotherapy apparatus 106. There is no need to provide the MRI control system 124 on the gantry 128 and a relatively simple data connection can be provided between the systems. The MRI system controller 124 can be in the same room as the off-gantry control system 300.

By providing the RT control system 216 on the gantry 218, the system can be operated continuously while the gantry 128 is rotated through more than 360 degrees. For most practical purposes, the gantry 128 can be considered to be unlimited in its rotation. However, it may be appropriate to limit the number of rotations in a particular direction before stopping to reconfigure the system.

Also, the on-gantry RT control system 200 is less susceptible to failure of the data links 210, 212 with the off-gantry control system 300. While basic commands can be provided from the off-gantry system 300 (such as start treatment sequence, interrupt or pause sequence, stop treatment, or system start up and shutdown sequences), as long as power is provided (via the slip ring 214), operation is not dependent on an active data from the off-gantry system 300 to the on-gantry system 200. Should this data link fail, the on-gantry system 200 can continue to operate as instructed, or can itself initiate pauses, stops, or shut downs, as appropriate.

The on-gantry control system 200 comprises a central controller which can store sets of instructions. Even if the data connection between the on-gantry control system 200 and the off-gantry control system 300 is severed, the radiotherapy apparatus 106 can continue to function because the on-gantry control system 200 has sufficient instructions and data to carry out the original treatment plan and has already sent instructions to the subsystems on the gantry.

Figure 1:
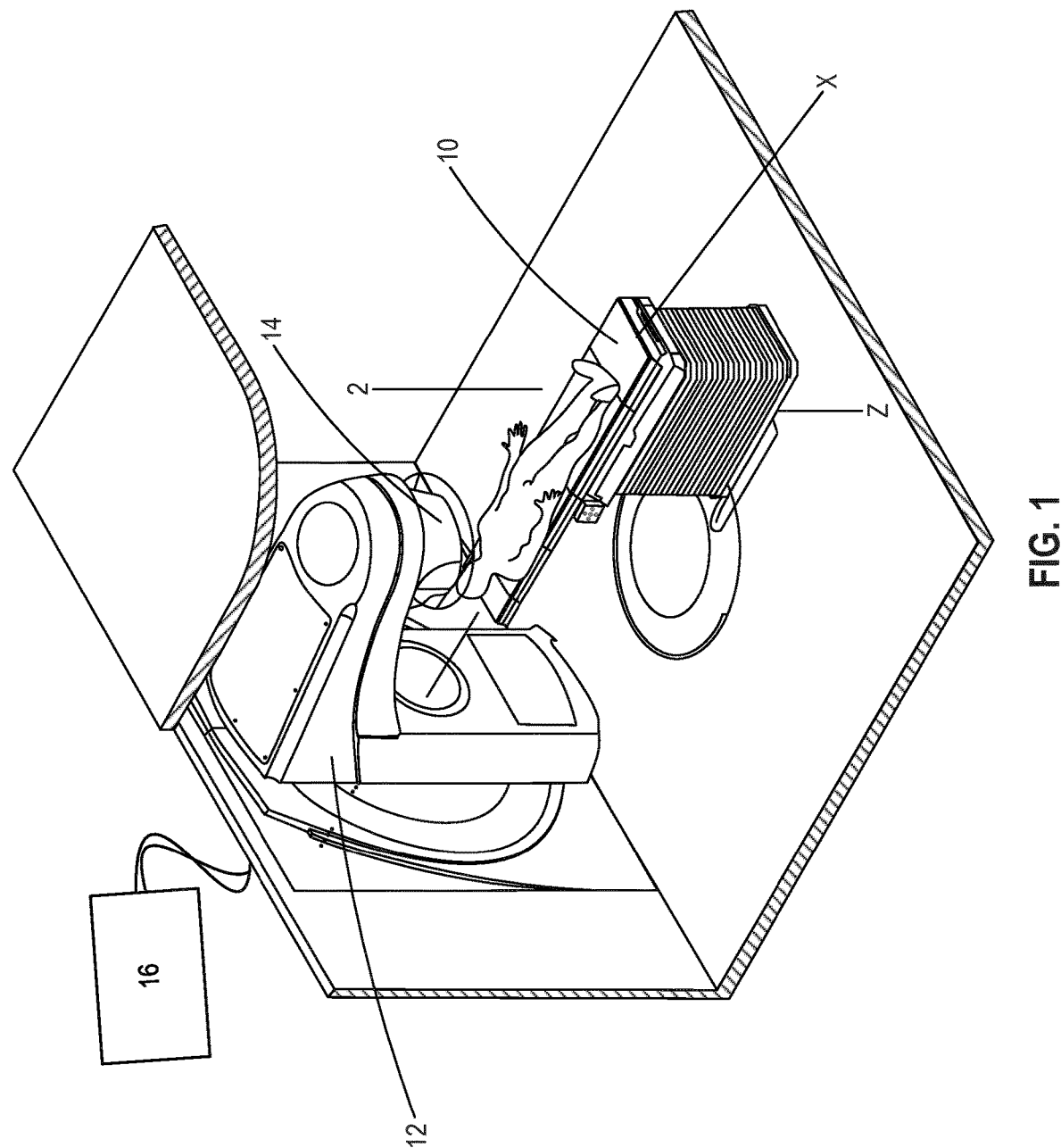
FIG. 1 is a known type of radiotherapy system.

While the control system is described above in relation to use with a combined MRI and radiotherapy system, it will be appreciated that it can be used for control of a radiotherapy system alone. Such a system may also be used with a radiotherapy system of the type shown in FIG. 1. In each case, providing the RT control system on the gantry allows rotation of the gantry though more than 360 degrees without the need to provide a high-bandwidth RT data link through the rotating mounting.

Further changes can be made within the scope of the invention.

The invention claimed is:

1. A radiotherapy system, comprising:
a patient support,
a radiation beam generator,
a gantry on which the radiation beam generator is mounted, the gantry being moveable so as to rotate the radiation beam generator around the patient support, and
a control system including:
a real-time control system mounted on the gantry and configured to provide real-time control signals to at least one of the patient support, the radiation beam generator, or the gantry to control the dynamic operational aspects of the radiation beam generator or the relative positioning of the patient support or the radiation beam generator; and
an off-gantry control system mounted separately from the gantry and configured to exchange control signals with the real-time control system mounted on the gantry via a data link,
wherein the real-time control system mounted on the gantry comprises a central controller which stores sets of instructions enabling the control system to continue to function in the event that the data link between the off-gantry control system and the real-time control system is severed;
wherein the off-gantry control system includes a treatment planning system that is configured to provide real-time control routines for implementation by the real-time control system mounted on the gantry, and wherein the off-gantry control system is operable to transmit control instructions to the real-time control system mounted on the gantry for storage in the central controller, the central controller being configured to store instructions such that the system can continue to implement the real-time control routines in the event that the data link between the off-gantry control system and the real-time control system is severed.

2. The radiotherapy system of claim 1, wherein the gantry comprises an annular structure having a bore through which the patient support can extend wherein the gantry is rotatable through more than 360° clockwise or anticlockwise about an axis extending through the bore.

3. The radiotherapy system of claim 2, wherein the annular gantry includes one or more slip rings through which power is provided for the radiation beam generator, and any other powered components mounted on the gantry, and which provides a data link with the real-time control system mounted on the gantry.

4. The radiotherapy system of claim 3, comprising separate slip rings for providing power and data.

5. The radiotherapy system of claim 1, wherein the real-time control system is configured to control generation and shaping of the beam generated by the radiation beam generator.

6. The radiotherapy system of claim 1, further comprising a wireless data connection between the real-time control system and the off-gantry control system.

7. The radiotherapy system of claim 1, further comprising a fibre-optic link between the off-gantry control system and the patient support to provide the real-time control signals from the real-time control system on the gantry.

8. The radiotherapy system of claim 1, wherein the off-gantry control system includes a gantry drive controller for controlling rotation of the gantry, wherein the real-time control system is configured to provide control signals to the gantry drive controller.

9. The radiotherapy system of claim 1, further comprising an imaging system on the gantry for obtaining images of a patient during treatment with the radiotherapy beam, the real-time control system being configured to provide control signals to the imaging system.

10. The radiotherapy system of claim 1, wherein the off-gantry control system is operable to generate control instructions comprising start treatment sequence instructions, interrupt or pause sequence instructions, stop treatment instructions, or system start up and shutdown instruction sequences whereas the real-time control system mounted on the gantry is operable to generate control sequences which the off-gantry control system is not operable to generate.

11. The radiotherapy system of claim 1, wherein the real-time control system mounted on the gantry is configured to initiate pauses, stops or shut downs in the event that the data link between the real-time control system mounted on the gantry and the off-gantry control system fails.

12. The radiotherapy system of claim 11, wherein the real-time control system is connected to components on the gantry via a hardwire data network, and the real-time control system is connected to components located off the gantry via the hardware link that provides a data signal path that extends through the slip ring.

13. A radiotherapy system, comprising:
a patient support;
a radiation beam generator;

a gantry on which the radiation beam generator is mounted, the gantry being moveable so as to rotate the radiation beam generator around the patient support;

a control system including a real-time control system mounted on the gantry and configured to provide real-time control signals to at least one of the patient support, the radiation beam generator, or the gantry; and a hardwire link that provides a data signal path between an off-gantry control system and the real-time control system mounted on the gantry, the data signal path extending through a slip ring on the gantry;

wherein the off-gantry control system includes a treatment planning system that is configured to provide real-time control routines for implementation by the real-time control system mounted on the gantry, and wherein the off-gantry control system is operable to transmit control instructions to the real-time control system mounted on the gantry for storage in a central controller, the central controller being configured to store instructions such that the system can continue to implement the real-time control routines in the event that the hardware link between the off-gantry control system and the real-time control system is severed.

14. The radiotherapy system of claim 13, wherein components on the gantry include the radiation beam generator, and components off the gantry include the patient support.

* * * * *